United States Patent [19]
Proctor

[11] 4,360,510
[45] Nov. 23, 1982

[54] METHOD FOR SCREENING ANTI-TUMOR AGENTS OF THE RETICULO-ENDOTHELIAL STIMULANT CLASS

[76] Inventor: Julian W. Proctor, 232 Village in the Park, 3000 Marshall Rd., Pittsburgh, Pa. 15214

[21] Appl. No.: 99,001

[22] Filed: Nov. 30, 1979

[51] Int. Cl.$^3$ .................... A61K 43/00; A61N 5/12
[52] U.S. Cl. .................... 424/1.5; 23/230.3; 128/659
[58] Field of Search ............... 424/1, 9, 1.5; 23/230.3; 128/659

[56] References Cited
PUBLICATIONS

Stiteler et al., J. Reticulo-Endothelial Soc., vol. 24, No. 6, Dec. 6, 1978, pp. 687–696.

Proctor et al., Cancer Treatment Reports, vol. 62, No. 11, Nov. 1978, pp. 1873–1880.

*Primary Examiner*—Leland A. Sebastian
*Attorney, Agent, or Firm*—Cushman, Darby & Cushman

[57] ABSTRACT

A procedure is disclosed for determining optimal doses, scheduling, routes of administration, the time for initiation, the magnitude and the duration of the anti-tumor effects, at various times following the administration to laboratory test animals such as rodents of doses of reticulo-endothelial stimulants by convenient anatomical routes. Following administration of the reticuloendothelial stimulant material the animals are challenged intravenously with radiolabelled tumor cells, and after 1 to 24 hours they are sacrificed, the lungs harvested and counted for radioactivity. The method allows for comparative studies on a number of agents and can be used as a screening assay as well as for the quality control of existing products.

4 Claims, 3 Drawing Figures

METHOD FOR SCREENING ANTI-TUMOR AGENTS OF THE RETICULO-ENDOTHELIAL STIMULANT CLASS

BACKGROUND OF THE INVENTION

Agents of the reticulo-endothelial stimulant class have been widely used in order to augment the systemic host defenses against cancer. The most commonly used preparations have been live bacteria, such as *Bacillus Calmette Guerin*—BCG, dead bacteria such as *Corynebacterium parvum* or derivatives (Methanol extract residue—MER). These preparations have several undesirable properties. They are toxic, immunogenic; leading to potentially lethal allergic sequelae; and in the case of BCG, infective. As a result, a number of analogues, some of them synthetic, usually based on the active principle of an existing agent, for instance Muramyl dipeptide from BCG and glucan from yeasts, have been developed which are potentially of low toxicity and which are neither infective nor immunogenic.

The selection of compounds and preparations for clinical use cannot be made in the clinic and are based on the results of studies both on their toxicity and their anti-tumor effects. The conventional tests for anti-tumor effects are either prophylactic, that is the preparation is administered prior to challenge with a tumor, or therapeutic, in which the agent is administered after challenge with a tumor, using inbred strains of laboratory animals, typically mice.

The tumor may be injected locally, such as subcutaneously, or systemically, usually intravenously, in which case the tumor grows in organs such as the lungs or liver, which are known as the target organs. Occasionally, the effect on the metastatic spread to distant organs, from a local implant, is analyzed. The parameters which are measured by such conventional tests are: incidence of tumor, number of tumors, weights of tumors, and volumes of tumors.

The most biologically relevant method explores therapeutic effects on spontaneous metastases. The most sensitive method uses prophylaxis against an intravenous challenge with tumor cells. The former is a difficult model to handle. It is insensitive, seldom reproducible, and involves either counting of lung nodules, which is subjective, weighing of tumor, which is imprecise, or planimetric analysis of serial histological sections which is impractically time consuming and takes up to 60 days to complete. The latter is easier to reproduce and more sensitive, but uses the same inadequate methods of analysis and takes over 30 days to complete.

Both methods are further limited by the spread of data which, within an experimental group, is large. For example, the data spread typically produces ranges of high:low values of 10:1 or greater and this allows for very poor definition. As a practical result this means that such testing procedures require large numbers of animals within each group usually greater than 10. Consequently the number of experimental groups is limited, and the amount of useful information that can be obtained is likewise severely restricted.

DETAILED DESCRIPTION OF THE INVENTION

Figure 1:
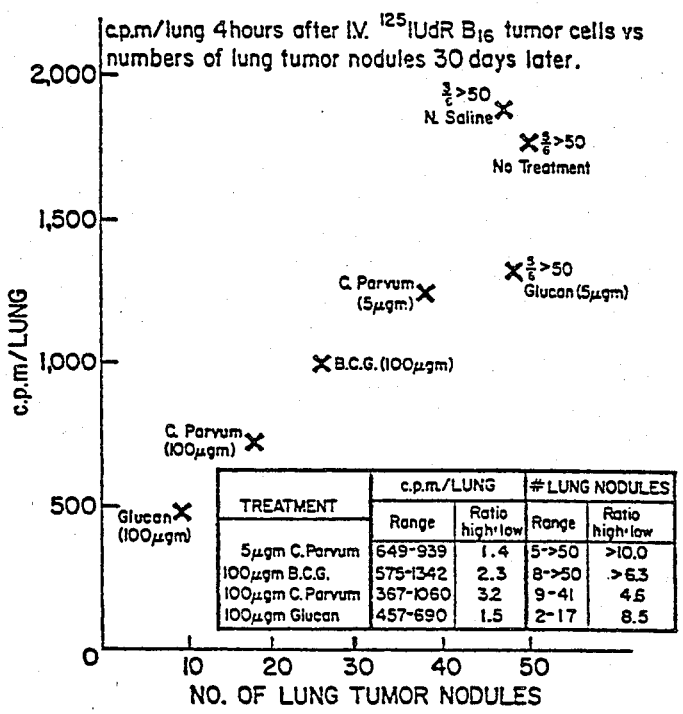
FIG. 1 is the counts per minute per lung 4 hours following intravenous injection of IUdR $B_{16}$ tumor cells plotted against the number of lung tumor nodules 30 days later.

According to my invention a process is disclosed in which the anti-tumor effects of reticulo-endothelial stimulants are assessed by administering such stimulants to laboratory animals, challenging the animals with a quantity of radiolabelled tumor cells, allowing the cells to grow and counting the animal lungs for radioactivity.

According to the method of my invention the radiolabelled cell bioassay requires five animals per group, can take as few as 2 to 4 hours to complete after tumor challenge, and produces data with a range of high:low values of 1.5:1–3.4:1. Examples of radiolabelled cell data versus data from the outgrowth of lung tumor nodules are shown in Table 1 and FIG. 1. Using the B16 tumor model, good correlations are found between the radiolabel assay results and those obtained by the prior method of visually assessing the outgrowth of pulmonary nodules.

TABLE 1

Comparisons of radioactivity/lung at four hours and the number of lung tumor nodules three weeks after injection of 125IOdR labelled B16 tumor cells

| Normal Controls | | Normal Saline | | B.C.G., Glaxo 5 gm | | B.C.G., Glaxo 200 gm | |
|---|---|---|---|---|---|---|---|
| c.p.m./ lung | No. of lung nodules | c.p.m./ lung | No. of lung nodules | c.p.m./ lung | No. of lung nodules | c.p.m./ lung | No. of lung nodules |
|  |  | 2538 |  |  |  | 12 |  |
| 2907 | 12 | 4300 |  | 13 | 4016 | 39 | 4737 9 |
| 3861 | 35 | 4330 |  | 28 | 4578 | 68 | 191717 |
| 5317 | 64 | 5815 |  | 57 | 6101 | 69 | 264521 |
| 5579 | 80 | 5856 |  | 79 | 6209 | 88 | 270522 |
| 5761 | 97 | 6357 |  | 96 | 6441 | 91 | 364933 |
| 7286 | 99 | 8561 |  | 103 |  |  |  |
| 5118.5 | 65.3 | 5393.7 | 62.7 | 5449.0 | 61.2 | 2530.6 | 17.8 |
| 2.5 | 8.3 | 3.4 | 7.9 | 1.6 | 7.6 | 2.1 | 6.6 |

| C. Parvum (Wellcome) | | | | Glucan (DiLuzio) | | | |
|---|---|---|---|---|---|---|---|
| c.p.m./ | No. of lung | c.p.m./ | No. of lung | c.p.m./ | No. of lung | c.p.m./ | No. of lung |

TABLE 1-continued

Comparisons of radioactivity/lung at four hours
and the number of lung tumor nodules three weeks after injection
of 125IOdR labelled B16 tumor cells

| lung | Nodules | lung | Nodules | lung | Nodules | lung | Nodules |
|---|---|---|---|---|---|---|---|
| 2271 | | | 604 | | | | |
| 2446 | 7 | | 713 | | 2 | 9 | 4 |
| 3313 | 17 | | 1307 | 2900 | 4 | 1650 | 5 |
| 4667 | 34 | | 1365 | 4262 | 40 | 1742 | 9 |
| 5276 | 36 | | 1623 | 4486 | 42 | 1906 | 18 |
| 6067 | 52 | | 1776 | 4557 | 61 | 2139 | 23 |
| 6476 | 72 | | 1935 | 5029 | 83 | 3383 | 31 |
| 4359.4 | 36.3 | 1331.9 | 8.7 | 4248.6 | 44.0 | 2164 | 15.0 |
| 1.5 | 10.3 | 3.2 | 10.5 | 1.7 | 9.2 | 2.1 | 7.8 |

As reported in the above table, mice were injected i.v. with various doses of DiLuzio Glucan, Glaxo BCG, or C. parvum on Day 0 and challenged with radiolabeled B16 cells on Day 8. Some were killed at 4 hours and the radioactivity of the lungs assessed on a gamma counter while the others were killed at 3 weeks and the numbers of lung nodules counted. The range of values are expressed as a ratio of High:Low.

In FIG. 1 mice were injected i.v. with various doses of DiLuzio Glucan, Glaxo BCG, or C. parvum on Day 0 and challenged with radiolabeled B16 cells on Day 8. Some were killed at 4 hours and the radioactivity of the lungs assessed on a gamma counter while the others were killed at 3 weeks and the numbers of lung nodules counted.

The range of values are expressed as a ratio of High:-Low except in cases in which the number and size of lung tumor nodules was too great for an analysis.

Using this procedure it was possible to establish optimum doses for the anti-tumor effects of C. parvum, three glucan compounds, three BCG compounds, a polymer (Lipopolysaccharide or LPS) and 9 muramyl dipeptide analogues. The time for initiation, the magnitude and duration of the anti-tumor response were established in a comparative fashion for Tice BCG, Di Luzio Glucan and muramyl corynedacterium bacterium parvum dipeptide.

Using this procedure it was also possible to rank 8 synthetic analogues of muramyl dipeptide in order to activity by performing three experiments on coded samples. The optimal doses for intravenous C. parvum and Di Luzio Glucan have been reproducible for more than ten consecutive experiments on each compound. Preliminary evidence strongly suggests that the predominant cause for the increased cell loss from the lungs of mice treated with anti-tumor agents of the recticulo-endothelial stimulant class is the death of said tumor cells rather than their redistribution to other organ sites.

As the test animals inbred mice or rats of 6–12 weeks of age are kept in a clean, stable environment and maintained on sterile tapwater and chow ad libitum.

The tumors used are either spontaneous tumors or those induced by viral, chemical or by X-ray from the above strain of origin, which will form tumor nodules in the lung after intravenous injection and which are capable of sustained clonogenic growth in tissue culture medium which is deficient in thymidine.

The tumor cells are labeled in the following manner: A sufficient concentration of tumor cells from an in vivo explant are plated in enriched tissue culture medium which is lacking in thymidine, but which contains antibacterial and fungal agents, fetal calf serum (10%) and a suitable concentration of a radiolabelled tritiated thymidine or 125 Iodo-deoxyuridine. The innoculated tissue culture medium is allowed to grow for 12–72 hours as may be required to develop a sufficient quantity of the cells and sufficient incorporation of the radiolabel. The cells are harvested mechanically or with EDTA and/or trypsin and washed at a time when cells register approximately 1 c.p.m./3–10 cells.

After administration of the agent or agents to be tested, a suitable number of radiolabelled tumor cells, for instance $10^5$, are injected intravenously, the animals sacrificed at a specified time point thereafter, the lungs harvested and counter for radioactivity on a suitable conter, $\beta$ for $^3H$ Thymidine, $\gamma$ for 125 Iodine.

Optimal doses and routes of administration were determined as follows:

Various doses of the reticulo-endothelial stimulants were injected either intravenously, intraperitoneally, intraorally, intrapleurally, or subcutaneously, and within 8 days thereafter the animals were challenged with the radiolabelled tumor cells as described above.

Figure 2:
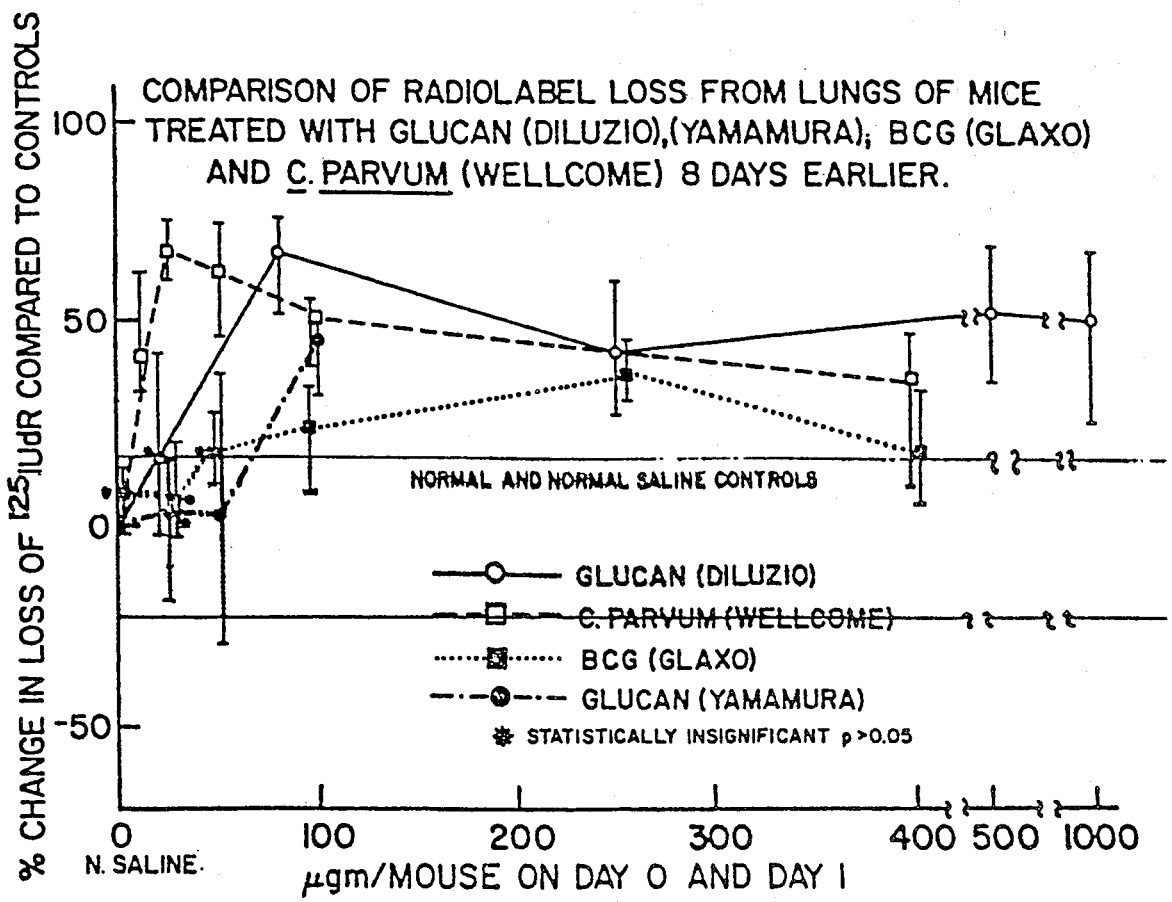
FIG. 2 is a comparison, as a function of dose, of radiolabel loss from lungs of mice treated with Glucan, BCG and C. parvum 8 days earlier.

Dose response curves were prepared, and an example is shown in FIG. 2, for glucan, C. parvum BCG. compared to normal and normal saline treated controls. The following optimum doses were defined for the intravenous rate of administration of these compounds, as outlined below, Wellcome C-parvum 25 μgm/mouse
Diluzio Glucan 50 μgm/mouse
Glaxo BCG 200 μgm/mouse in the DBA2 TS1699 mouse mammary carcinoma and the C57BL6J B16 mouse melanoma systems.

The kinetics of tumor cell clearance have been shown to increase within 2 hours of injection of the radiolabelled tumor cells, 8 days after administration of C. parvum, Glucan and BCG.

Following administration of Wellcome C. parvum or Glaxo BCG or Diluzio Glucan, by challenging animals between two and 60 days thereafter and performing the assay, it has been possible to define the time required for initiation of the anti-tumor effect, the magnitude of the anti-tumor effect and the duration of the anti-tumor effect.

Statistical analysis was done as follows: A non-parametric ranking method of Mann Whitney was used.

This procedure can be used to screen anti-tumor agents of the reticuloendothelial stimulant category, and once these are established for clinical use, as a quality control measure to test the reproducibility within a batch of a compound, and of one batch with another.

Figure 3:
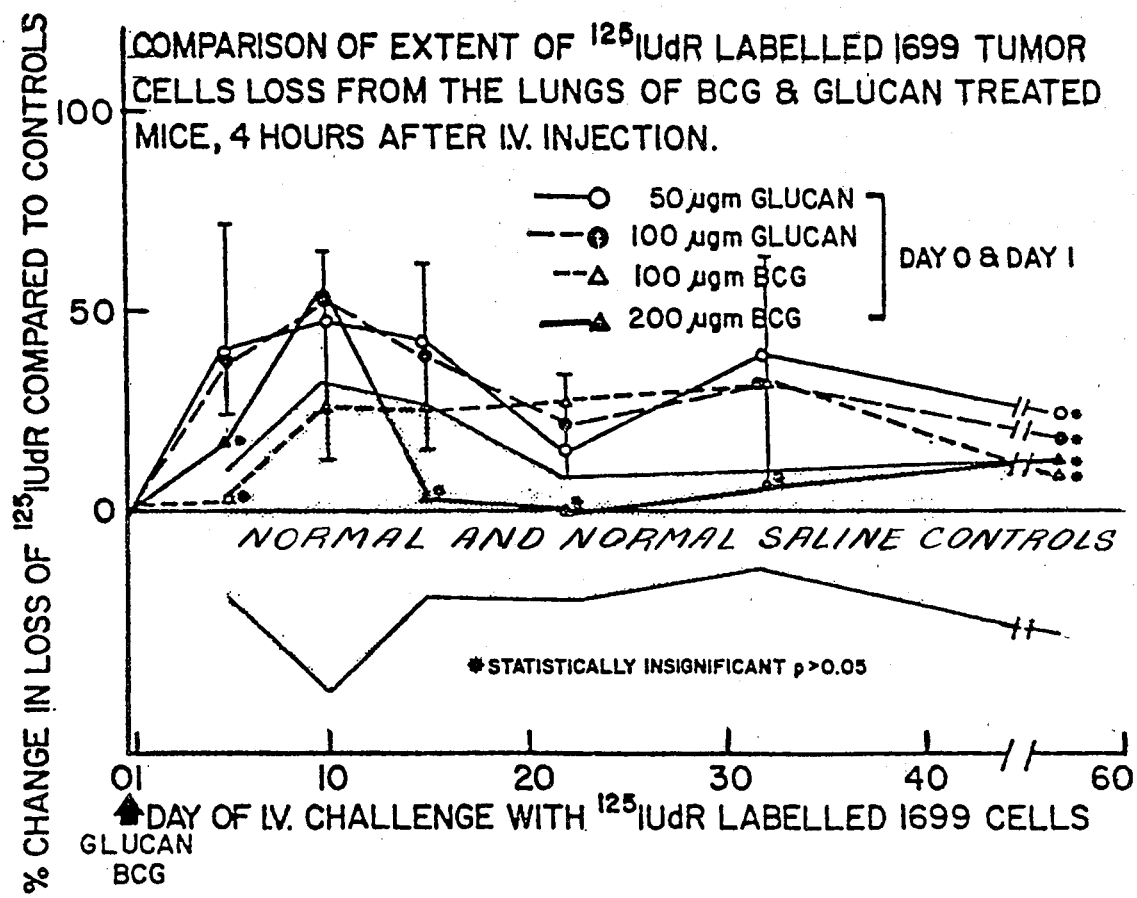
FIG. 3 is a comparison of the extent of intravenously injected $^{125}$IUdR labelled 1699 tumor cell loss from the lungs, at 4 hours of mice treated with BCG and Glucan, as a function of time after the BCG and glucan administration.

FIG. 3. Shaded areas range of values for normal and normal saline-treated control mice. Vertical bars range of values for the change in lung radioactivity, expressed as a percentage of the mean value for the controls, of all groups of mice in which there was a statistically significant difference compared to the controls at P 0.05 level. Mice were injected iv with 2 doses of either DiLuzio or Yamamura glucan, C. parvum, BCG or normal saline on Days 0 and 1. They were challenged with 10 radiolabeled T1699 cells at various points thereafter and were killed 4 hours later, and the lungs were harvested and counted on a gamma counter.

The radiolabelled tumor cell assay procedure of my invention can establish optimal doses, optimal routes of administration, optimal dose scheduling, the time for initiation of anti-tumor effects, the duration of anti-tumor effects and the magnitude of anti-tumor effects of anti-tumor agents of the reticulo-endothelial stimulant class and has the following advantages over previously published methods. The method requires few animals (less than one half), provides better definition, up to 3-5 times, provides precise and objective measured data and takes a fraction of the time to complete, in the order of 4 hours versus 30 to 60 days.

The procedure has been shown to constitute a rapid, cheap, reproducible and biologically relevant assay which can generate data that could not be obtained on a practical basis by existing methods.

I claim:

1. A method for determining the anti-tumor activity of an agent of the reticulo-endothelial stimulant class comprising the sequential steps of:
   (1) administering predetermined doses of an anti-tumor agent of the reticulo-endothelial stimulant class to a rodent, by a suitable route of administration;
   (2) at between 2 and 60 days, thereafter, administering a predetermined quantity of radiolabelled tumor cells, radiolabelled with a DNA label, to said rodent;
   (3) allowing the administered radiolabelled tumor cells to build up in the lung and subsequently allowing at least about 50% of said cells to be lost from the lung of said rodent;
   (4) isolating the lung tissue from said rodent and measuring the radioactivity emanating from the remaining radiolabelled tumor cells in said isolated piece of tissue; and thereafter
   (5) calculating the increase in loss of said radioactivity from said isolated piece of lung tissue of a predetermined size from animals treated with said anti-tumor agent of the reticulo-endothelial stimulant class, compared with the loss of radioactivity from a piece of lung tissue of substantially the same predetermined size isolated from rodents receiving no or a placebo treatment, the increase representing an index of the magnitude of the anti-tumor effect observed.

2. The method according to claim 1 wherein said anti-cancer agents are selected from the group consisting of C. parvum, glucans, BCG's and muramyl dipeptides.

3. The method according to claim 1 wherein the injected tumor cells are allowed to disappear from the lung for a period of time from one to within 24 hours before the lung tissue is isolated in step (4).

4. A method for determining the anti-tumor activity of an agent of the reticulo-endothelial stimulant class comprising the sequential steps of:
   (1) administering predetermined doses of an anti-tumor agent of the reticulo-endothelial stimulant class to a rodent by a suitable route of administration, said agent selected from the group consisting of C. parvum, glucan compounds, BCG compounds, Lipopolysaccharide, muramyl dipeptides, and NVE's;
   (2) at between 2 and 60 days, thereafter, administering a predetermined quantity of radiolabelled tumor cells, radiolabelled with a DNA label, to said rodent;
   (3) allowing the administered radiolabelled tumor cells to build up in the lung and subsequently allowing at least about 50% of said cells to be lost from the lung of said rodent;
   (4) isolating the lung tissue from said rodent and measuring the radioactivity emanating from the remaining radiolabelled tumor cells in said isolated piece of tissue; and thereafter
   (5) calculating the increase in loss of said radioactivity from said isolated piece of lung tissue of a predetermined size from animals treated with said anti-tumor agent of the reticulo-endothelial stimulant class, compared with the loss of radioactivity from a piece of lung tissue of substantially the same predetermined size isolated from rodents receiving no or a placebo treatment, the increase representing an index of the magnitude of the anti-tumor effect observed.

* * * * *

Disclaimer 4,360,510.—*Julian W. Proctor*, Pittsburgh, Pa. METHOD FOR SCREENING ANTI-TUMOR AGENTS OF THE RETICULO-ENDOTHELIAL STIMULANT CLASS. Patent dated Nov. 23, 1982. Disclaimer filed May 31, 1983, by the inventor.

Hereby enters this disclaimer to claim 4 of said patent.

[*Official Gazette July 19, 1983.*]